United States Patent [19]

Tomita et al.

[11] Patent Number: 5,389,611
[45] Date of Patent: * Feb. 14, 1995

[54] LACTOFERRIN HYDROLYZATE FOR USE AS AN ANTIBACTERIAL AGENT AND AS A TYROSINASE INHIBITION AGENT

[75] Inventors: Mamoru Tomita, Yokohama; Kouzou Kawase, Urawa; Yoshitaka Tamura, Yokohama; Mitsunori Takase, Ohmiya; Hiroshi Miyakawa; Koji Yamauchi, both of Kamakura; Hitoshi Saito, Kawasaki; Hiroaki Abe, Yokosuka; Seiichi Shimamura; Susumu Kobayashi, both of Yokohama, all of Japan

[73] Assignee: Morinaga Milk Industry Co., Ltd., Tokyo, Japan

[*] Notice: The portion of the term of this patent subsequent to May 25, 2010 has been disclaimed.

[21] Appl. No.: 803,955

[22] Filed: Dec. 9, 1991

Related U.S. Application Data

[62] Division of Ser. No. 634,763, Dec. 27, 1990, Pat. No. 5,214,028.

[30] Foreign Application Priority Data

Jan. 23, 1990 [JP] Japan ................................ 2-13315
Jun. 26, 1990 [JP] Japan ................................ 2-169636

[51] Int. Cl.$^6$ ............................ C07K 3/10; C07K 1/12
[52] U.S. Cl. ........................................ 514/6; 426/656; 426/657; 514/2; 514/12; 514/21; 530/395; 530/407; 435/68.1

[58] Field of Search ................. 405/68.1; 514/2, 12, 514/21; 530/395, 407

[56] References Cited

U.S. PATENT DOCUMENTS

| | | |
|---|---|---|
| 4,668,771 | 5/1987 | Kawakami et al. . |
| 4,791,193 | 12/1988 | Okonogi et al. . |
| 4,918,008 | 4/1990 | Gauri ............................ 435/68.1 |
| 4,997,914 | 3/1991 | Kawakami et al. . |
| 5,214,028 | 5/1993 | Tomita et al. ........................ 514/6 |

FOREIGN PATENT DOCUMENTS

62-249931 10/1987 Japan .

OTHER PUBLICATIONS

Suzuki et al., *Agric. Biol. Chem.*, vol. 53(6), pp. 1705–1706 (1989).
Spik et al., *Biochimie*, vol. 70 (1988), pp. 1459–1469.
Stryer, "Biochemistry," 3rd Ed. (1988), pp. 202–211.
Tomita et al, J. Dairy Sci. 74:1437–1442 (1991).

*Primary Examiner*—Howard E. Schain
*Attorney, Agent, or Firm*—Oblon, Spivak, McClelland, Maier & Neustadt

[57] ABSTRACT

Lactoferrin hydrolyzates, having a decomposition rate between 6%–20% as measured by formol titration, for use as an antibacterial agent, and which have remarkably more potent activity than unhydrolyzed lactoferrin; and lactoferrin hydrolyzates, having a decomposition rate between 4–50% as measured by formol titration, for use as a tyrosinase inhibition agent, are obtainable by conventional methods for hydrolysis with acids or enzymes, and are stable to heating.

11 Claims, No Drawings

LACTOFERRIN HYDROLYZATE FOR USE AS AN ANTIBACTERIAL AGENT AND AS A TYROSINASE INHIBITION AGENT

The present application is a divisional application of application Ser. No. 07/634,763, filed Dec. 27, 1990, now U.S. Pat. No. 5,214,028.

FIELD OF THE INVENTION

The present invention relates to lactoferrin hydrolyzate for use as an antibacterial agent and as a tyrosinase inhibition agent. In other words, the present invention relates to an antibacterial and/or tyrosinase inhibition agent consisting of or containing lactoferrin hydrolyzate as the effective components.

BACKGROUND OF THE INVENTION

Lactoferrin is known as an iron-binding protein occurring in lacrima, saliva, peripheral blood, milk and the like. It is known that lactoferrin has antibacterial activity against coliform *bacillus* (*Escherichia coli*), staphylococcus and other enterobacteria (or enteric bacteria) in a concentration within the range of 0.5–30 mg/ml (Nonnecke, B. J. and Smith, K. L.; Journal of Dairy Science; Vol. 67, pp. 606; 1984).

It has been considered in general that the antibacterial activity of lactoferrin is derived from the situation wherein environmental iron becomes unavailable to those microorganisms which require iron strongly, due to the chelation of lactoferrin with environmental iron. The antibacterial activity of lactoferrin is not necessarily strong enough, thus a considerable quantity of lactoferrin is required to utilize its antibacterial activity, especially when lactoferrin is added to, impregnated into, adhered to, or coated onto other materials. Thus, there is a limitation of its usefulness as an antibacterial agent.

It has been attempted to increase the antibacterial activity of lactoferrin. For example, it has been proposed to use lactoferrin together with lysozyme (Japanese Unexamined Patent Application Gazette No. 62(1987)-249931). It has been also reported that the copresence of lactoferrin and secretory IgA may multiplicatively augment antibacterial activity of the former (S. Stephens, J. M. Dolby, J. Montreuil and G. Spik; Immunology; Vol. 41; Page 597; 1980).

To the best knowledge of the inventors, however, there has been no report indicating that chemical treatment of lactoferrin may improve its antibacterial activity.

It is also known that lactoferrin is unstable to heating, and that the antibacterial activity of lactoferrin can be almost completely suppressed by heating it at 62.5° C. for 30 minutes, and complete deactivation is achieved by heating it at 70° C. for 15 minutes (Ford, J. E. et al; Journal of Pediatrics, Vol. 90, page 29; 1977).

Therefore, sufficient thermal treatment cannot be applied to those materials which contain lactoferrin as an antibacterial agent.

Also, it is known that lactoferrin is not stable to pH variation.

The inventors of the present invention have exerted their efforts to increase the antibacterial activity of lactoferrin and to improve its stability to heating, and found that hydrolyzates of lactoferrin substances such as native lactoferrin, apolactoferrin, metal saturated lactoferrin, and mixtures thereof show much stronger antibacterial activity and superior stability to heating than unhydrolyzed lactoferrin. The present invention is based on this discovery. The words "native lactoferrin" used herein means that lactoferrin was just isolated from milk and the like, and that no chemical treatment such as iron removing and chelation with metals is made thereon.

Meanwhile it has not been known that lactoferrin and its hydrolyzates have potent tyrosinase inhibition activity.

Tyrosinase is known as an enzyme which may act as a catalyst for the oxidization of tyrosine, and other monohydric phenols and corresponding dihydric orthophenols with molecular oxygen. Tyrosinase widely occurs in plants such as mushrooms, potatoes, apples as well as in animal tissues. It is also known that tyrosinase is related to darkening phenomena at an injured portion of plant tissue, and is also related to the formation of melanin pigment in various tissues of animals, especially in epidermal cells (Editorial Committee of Encyclopedia Chimica, Encyclopedia Chimica, Vol. 5, page 976, Kyohritsu Shuppan; 1960).

It is also known that pigmentation of melanin in epidermal cells or mucous membranes in Addison's disease results from a decrease in secretion of adrenal cortex hormones which antagonize melanotropin which in turn promotes tyrosinase activity (Editorial Committee of Encyclopedia Chimica, Encyclopedia Chimica, Vol. 1, Page 65, Kyohritsu Shuppan; 1960).

Therefore, it has been strongly desired, in the industrial fields of pharmaceuticals, cosmetics, food and the like, to develop a tyrosinase inhibition agent for prevention and therapy of symptoms resulting from undesirable effects of tyrosinase activity. Especially in the cosmetics industry, research has been actively made on cosmetics or medicines for external use for effective inhibition of melanin-formation and for whitening of skin, and many products containing tyrosinase inhibition agents have been successively developed. There are known many tyrosinase inhibition agents, for example, cysteine and vitamin C (Yutaka Mishima et al, Fundamental Dermatology, page 258, Asakura Shoten; 1973), kojic acid (Nikkei Sangyo Newspaper, May 24th 1988), arbutin (Ken-ichi Tomita, Preliminary Text for 20th F. J. Seminar, page 21, Fragrance Journal Company, Mar. 14, 1990), products of microorganism belonging to the genus of Trichoderma (Unexamined Japanese Patent Application Gazette No. 2(1990)-145189).

The conventional tyrosinase inhibition agents, however, had more or less defects in that they are unstable in the products, they are excessively potent to melanocytes which produce melanin pigment, they are too expensive due to the difficulty in obtaining their raw materials, and they are not usable as cosmetics or medicines for external use from the view points of safety, economics, preservability, reliability for whitening effect and so on.

The inventors of the present invention found that lactoferrin, especially its hydrolyzate, has potent tyrosinase-inhibition activity. The present invention is also based on this discovery.

OBJECTS OF THE INVENTION

Therefore, it is an object of the present invention to provide lactoferrin hydrolyzate for use as an antibacterial agent.

More particularly, it is an object of the present invention to provide an antibacterial agent consisting of lactoferrin hydrolyzate as the effective component.

It is another object of the present invention to provide antibacterial agent comprising an effective amount of lactoferrin hydrolyzate as an effective component.

It is a still further object of the present invention to provide various products containing the antibacterial and/or tyrosinase inhibition agent.

It is a further object of the present invention to provide a method for treating materials with said antibacterial agent.

It is another object of the present invention to provide lactoferrin hydrolyzate for use as a tyrosinase inhibition agent.

It is a further object of the present invention to provide a tyrosinase inhibition agent consisting of lactoferrin hydrolyzate.

It is a still further object of the present invention to provide tyrosinase inhibition agent comprising an effective amount of lactoferrin hydrolyzate as an effective component.

It is a further object of the present invention to provide various types of products comprising an effective amount of lactoferrin hydrolyzate as a tyrosinase inhibition agent.

SUMMARY OF THE INVENTION

In accordance with one aspect of the present invention, lactoferrin hydrolyzate can be used as an excellent antibacterial agent. Preferable ranges in the decomposition rate of lactoferrin hydrolyzate for use as an antibacterial agent are 6–20%, especially 7–15%, as measured by the formol titration method (percentage of formol nitrogen to total nitrogen).

In accordance with the other aspect of the present invention, lactoferrin hydrolyzate can be used as a tyrosinase inhibition agent. Preferable ranges in the decomposition rate of lactoferrin hydrolyzates for use as a tyrosinase inhibition agent are 4–50%, especially 6–40%, as measured by the same method.

Lactoferrin hydrolyzate can be prepared by conventional methods (for example, hydrolysis of lactoferrin by organic or inorganic acids or by enzymes).

Any lactoferrin substance can be used as the starting material for preparation of lactoferrin hydrolyzate, for example, lactoferrin obtainable in the market, native lactoferrin just isolated by conventional methods (for example, ion-exchange chromatography) from mammalian milk, apolactoferrin obtainable by removing iron from native lactoferrin with hydrochloric acid, citric acid and the like, metal saturated lactoferrin obtainable by chelating apolactoferrin with iron, copper, zinc, manganese and the like, or a mixture thereof (hereinafter these lactoferrin substances are abbreviated as LF).

Any mammalian milk (for example, human breast milk as well as cow's, sheep's, goat's, horse's milk and the like) at any lactation stage (for example, colostrum, transitional milk, matured milk, milk in later lactation) can be used as the source of LF. Furthermore, processed milk or byproducts in milk-processing such as skim milk, whey and the like can be used as the source of lactoferrin (hereinafter they are referred to as milk and the like).

Acid hydrolysis can be performed in accordance with conventional methods. For example, LF is dissolved into water or purified water in a concentration within the range of 0.1–20% (by weight, the same will be applied otherwise indicated), preferably 5–15%, followed by pH adjustment of the resultant solution to 1–4, preferably to 2–3, and hydrolysis reaction at a proper temperature depending upon the pH of the solution. For instance, when the pH is adjusted to 1–2, the solution is heated at 80°–130° C., preferably at 90°–120° C.; when the pH is adjusted to 2–4, the solution is heated at 100°–130° C., preferably at 100°–120° C.; respectively for 1–120 minutes, preferably 5–60 minutes until the decomposition rate (by formol titration) of the LF hydrolyzate is 6–20%, preferably to 7–15%.

Enzymatic hydrolysis can be performed in accordance with conventional methods. For example, LF is dissolved into water or purified water in a concentration between 0.5–20%, preferably 5–15%, followed by pH adjustment of the resultant solution into the optimum pH range, and enzymatic hydrolysis is then conducted under proper conditions; for example, a temperature between 15°–55° C., preferably between 30°–50° C. for 30–600 minutes, preferably for 60–300 minutes. The reacted mixture is neutralized, followed by deactivation of the enzyme in accordance with conventional methods.

In the case of the preparation of an antibacterial agent, any acidic enzymes such as MOLSIN F (trademark; by Seishin Seiyaku; optimum pH.: 2.5–3.0), swine pepsin (by Wakoh Junyaku Kogyo; optimum pH: 2–3), SUMIZYME AP (trademark; by Shin Nihon Kagaku; optimum pH: 3.0), AMANO M (trademark; by Amano Seiyaku; optimum pH: 3.0) and the like can be used individually or in any combination thereof. Among them, good results are obtained by use of swine pepsin and SUMIZYME AP.

In the case of the preparation of a tyrosinase inhibition agent, there is no limitation to the enzymes to be used. For example, Amano A (trademark, by AMANO Seiyaku; optimum pH: 7.0), trypsin, exopeptidase originating from lactic acid bacteria recited in Japanese Examined Patent Application Gazette No. 48(1973)-43878 and commercial SHOHYU-ENZYME (soy sauce enzyme) comprising exopeptidase (by Tanabe Seiyaku) can be used, in addition to those enumerated above, individually or in any combination thereof.

The quantity of enzymes to be used may be 0.1–5.0%, preferably 0.5–3.0% to the substrate used.

Regardless of the method of hydrolysis, the resultant solution containing LF hydrolyzate is cooled by conventional methods, if necessary, followed by neutralization, demineralization, and decolorization. The resultant solution can be used as a liquid product as it is or if required, the solution is further concentrated and/or dried to obtain a concentrated liquid product or a powdery product.

The conditions of hydrolysis referred to above are not critical, but can be modified depending upon the temperature, the period of time, the pressure as well as the kind and quantity of the acid or enzyme used.

The LF hydrolyzate to the present invention is a mixture of the decomposed substances having different molecular weights.

Thus obtained LF hydrolyzate is highly stable to heating, and is excellent in antibacterial activity compared to unhydrolyzed lactoferrin, and has tyrosinase inhibition activity.

DETAILED DESCRIPTION OF THE INVENTION

Now some tests will be described hereunder for exemplifying the utility of LF hydrolyzate as an antibacterial agent.

[TEST 1]

The purpose of this test is to show relationships between the decomposition rate of LF hydrolyzate and antibacterial activity.

1) Method 1-1) Preparation of Samples

Native LF sold in the market (by Oleofina, Belgium) was dissolved into purified water in 5% concentration. The resultant solution was divided into several lots which were adjusted into different pH, 1, 2, 3 and 4 by adding 1M hydrochloric acid thereto. The resultant solutions having different pH were subjected to hydrolysis reaction under different conditions in a combination of a temperature between 60°–130° C. and a time between 5–60 minutes to thereby prepare samples of LF hydrolyzate having different decomposition rates as shown in Table 1.

1-2) Measurement of Hydrolyzation Rate

The decomposition rate (%) of the resultant LF hydrolyzate was determined in such a manner that the quantity of formol nitrogen in the respective samples was measured by formol titration method, then the resultant values were applied to the following formula:

$$\text{decomposition rate } (\%) = 100 \times (A/B)$$

(wherein A denotes the quantity of formol nitrogen, and B denotes the quantity of total nitrogen).

1-3) Preparation of Pre-culture and Culture Medium 1-3-1) Preparation of Pre-culture From the stock culture of *Escherichia coli*, a loop of bacterial cells was taken out with a platinum loop and smeared onto a standard plate agar medium (by Nissui Seiyaku), followed by incubation at 35° C. for 16 hours under aerobic condition. The colonies grown on the surface of the culture were collected with a platinum loop and suspended into sterilized saline solution to prepare pre-culture having optical density of 1.0 (at 660 nm) measured by a spectrophotometer (by Hitachi Seisakusho).

1-3-2) Preparation of Basic Culture Medium

Basic culture medium (liquid culture medium) was prepared by dissolving bactocasitone (by Difco) into purified water in 1% concentration, adjusting the pH of the resultant solution to 7.0 with 1M sodium hydroxide, then sterilizing at 115° C. for 15 minutes.

1-3-3) Preparation of Test and Control Culture Media

The solutions of LF hydrolyzates previously prepared in item 1-1) were respectively filtered with membrane filters (by Advantech) to remove microorganisms which might be included therein. Different quantities of each of filtered solutions of LF hydrolyzates were respectively added to a portion of the basic culture medium to give 6 lots of test culture media containing LF hydrolyzate in different concentrations for each LF hydrolyzate having different decomposition rates as shown in Table 1. Control culture media containing unhydrolyzed LF in different concentrations were also prepared in the same manner as in the test culture media.

1-3-4) Test for Antibacterial Activity

To each of the test and control culture media, the pre-culture was inoculated in 1% concentration, followed by incubation at 35° C. for 16 hours. The proliferation inhibition rate was determined by measuring the optical density of the culture broth in the same manner as previously described and calculating in accordance with the following formula:

$$\text{proliferation inhibition rate } (\%) = 100 - (A/B \times 100)$$

(wherein A denotes the difference of optical densities of the test culture media before and after 16 hours incubation, B denotes the difference of optical densities of the control culture media before and after 16 hours incubation respectively) and 2) Results of the Test The results are shown in Table 1.

TABLE 1

| decomposition rate (%) | concentration (ppm) | | | | | |
|---|---|---|---|---|---|---|
| | 25 | 50 | 100 | 250 | 500 | 1000 |
| control | 0 | 0 | 0 | 16 | 42 | 65 |
| 6 | 8 | 26 | 40 | 94 | 100 | 100 |
| 7 | 17 | 41 | 98 | 100 | 100 | 100 |
| 8 | 21 | 60 | 100 | 100 | 100 | 100 |
| 9 | 28 | 69 | 100 | 100 | 100 | 100 |
| 10 | 23 | 74 | 100 | 100 | 100 | 100 |
| 11 | 18 | 59 | 100 | 100 | 100 | 100 |
| 12 | 11 | 45 | 100 | 100 | 100 | 100 |
| 13 | 4 | 40 | 94 | 100 | 100 | 100 |
| 14 | 2 | 38 | 86 | 100 | 100 | 100 |
| 15 | 0 | 16 | 73 | 97 | 100 | 100 |
| 16 | 0 | 9 | 47 | 84 | 96 | 100 |
| 18 | 0 | 2 | 32 | 68 | 89 | 100 |
| 20 | 0 | 0 | 20 | 56 | 82 | 93 |
| 25 | 0 | 0 | 2 | 9 | 25 | 60 |
| 30 | 0 | 0 | 0 | 0 | 1 | 5 |

Note: the values indicate proliferation inhibition rates (%).

As will be seen from the Table 1, the unhydrolyzed LF (control) showed antibacterial activity when more than 250 ppm of LF was added, but complete inhibition could not be achieved even when 1000 ppm of LF was added (weak antibacterial activity). In contrast to this, LF hydrolyzate having a 10% decomposition rate showed potent antibacterial activity at the concentration of 25 ppm, and proliferation of *E. coli* was completely inhibited at a concentration over 100 ppm. It will be understood that LF hydrolyzates of a decomposition rate between 6–20%, especially between 7–15%, prepared by acid hydrolysis of LF have remarkably potent antibacterial activity in comparison with unhydrolyzed LF.

[TEST 2]

Ten samples of powdery LF hydrolyzates, nos. 1–10, were prepared by the following procedure: each of 5 kinds of commercial enzymes was added to 5% aqueous solution of commercial LF (by Oleofina), followed by adjustment of the pH to the optimum pH of the respective enzymes, enzymatic hydrolysis at 37° C. for different reaction times, adjustment of the pH of the hydrolyzed solutions to 7, deactivation of the enzymes at 80° C. for 10 minutes, and lyophilization of the resulting solutions. The kinds of enzymes and their quantities added to the substrate (LF), reaction times of hydrolysis and decomposition rates of the respective samples are shown in Table 2. The decomposition rates were determined by the same method as in Test 1.

2) Result

The results of this test are shown in Table 2.

TABLE 2

| sample No. | enzymes used | quantity of enzyme (%) | reaction time (minutes) | decomposition rate (%) |
|---|---|---|---|---|
| 1 | MOLSIN F | 0.1 | 120 | 12.4 |
| 2 | MOLSIN F | 1.0 | 300 | 14.7 |
| 3 | swine pepsin | 0.3 | 30 | 6.3 |
| 4 | swine pepsin | 3.0 | 180 | 11.4 |
| 5 | SUMIZYME AP | 1.0 | 180 | 10.3 |
| 6 | SUMIZYME AP | 3.0 | 180 | 13.5 |
| 7 | AMANO M | 0.1 | 60 | 5.9 |
| 8 | AMANO M | 3.0 | 120 | 12.6 |
| 9 | Trypsin | 3.0 | 180 | 10.3 |
| 10 | Trypsin | 6.0 | 360 | 12.5 |

As will be seen from Table 2, decomposition rates of LF hydrolyzate by acidic proteases such as MOLSIN F, swine pepsin, SUMIZYME AP, and AMANO M fall between 5.9-14.7%, and those by trypsin which is a neutral protease were 10.3-12.5%.

[TEST 3]

The purpose of this test is to exemplify the antibacterial activity of LF hydrolyzate prepared by acid hydrolysis.

Antibacterial activity against *E. coli* of LF hydrolyzate having a 12% decomposition rate prepared in the same manner as in Example 2 (hydrolysis by citric acid) and that of unhydrolyzed LF were determined in the same manner as in Test 1.

The results are shown in Table 3.

TABLE 3

| sample | quantity added (ppm) | | | | | |
|---|---|---|---|---|---|---|
| | 25 | 50 | 100 | 250 | 500 | 1000 |
| unhydrolyzed LF | 0 | 0 | 5 | 16 | 74 | 85 |
| LF hydrolyzate | 12 | 41 | 100 | 100 | 100 | 100 |

Note: The values indicate proliferation inhibition rates (%).

From the results of the foregoing test, it is exemplified that LF hydrolyzate prepared by organic acid hydrolysis, and inorganic acid hydrolysis have antibacterial activity.

[TEST 4]

The purpose of this test is to exemplify the effectiveness of the method for treatment of a material with antibacterial agent in accordance with the present invention.

A quantity of sliced vegetables sold in the market was divided into three parts. Each of the parts was respectively dipped into a 1% aqueous solution of LF hydrolyzate prepared in the same manner as in Example 1 (hydrolyzed by inorganic acid, decomposition rate: 9%), unhydrolyzed LF solution (control) and sterilized water (control) for 30 seconds. Each of the treated samples was drained then preserved at 5° C. for observation. Viable bacterial count of the samples was periodically determined by the conventional method.

The results of this test are shown in Table 4.

TABLE 4

| Samples | preservation period (hours) | | | |
|---|---|---|---|---|
| | 0 | 12 | 24 | 36 |
| sterilized water | $5.1 \times 10^3$ | $4.9 \times 10^4$ | $5.0 \times 10^5$ | $9.2 \times 10^5$ |
| unhydrolyzed LF | $5.1 \times 10^3$ | $2.0 \times 10^4$ | $1.8 \times 10^5$ | $2.2 \times 10^5$ |
| LF hydrolyzate | $5.1 \times 10^3$ | $1.1 \times 10^3$ | $1.5 \times 10^3$ | $1.6 \times 10^3$ |

Note: The values indicate viable bacterial counts per 1 g of sliced vegetables.

As will be seen from the Table 4, it is exemplified that LF hydrolyzate has remarkably stronger antibacterial activity than unhydrolyzed LF when they are used for treatment of materials.

[TEST 5]

The purpose of this test is to exemplify the effectiveness of inclusion of LF hydrolyzate in a food as the effective component for antibacterial activity.

A quantity of raw milk was sterilized at 65° C. for 30 minutes and dispensed into test tubes in 10 ml amounts. To each of the test tubes, LF hydrolyzate having a 9% decomposition rate (prepared in Example 1) or unhydrolyzed LF were added and homogeneously mixed in 0.1% concentration, and sealed to prepare samples No. 1 and No. 2. A sample which contains raw milk only was prepared as a control sample. These samples were preserved at 25° C. to determine preservable days during which coagulation of raw milk was not observed.

The results were that coagulation was observed in sample No. 1 on the 9th day, in sample 2 on the 4th day, and in the control sample on the 2nd day. This means that LF hydrolyzate has excellent antibacterial activity. Meanwhile, an organoleptic test was carried out with respect to the control sample and sample No. 1 immediately after preparation of the samples, and confirmed that there was no difference in taste and appearance therebetween.

[TEST 6]

The purpose of this test is to exemplify antibacterial activity of LF hydrolyzate prepared by enzymatic hydrolysis.

1) Method

Aqueous solutions of 10 kinds of LF hydrolyzate (prepared using different enzymes) and an aqueous solution of unhydrolyzed LF prepared in the same manner as in test 2 were filtered with membrane filters (by Advantec) to remove bacterial cells which might be contaminated therein. Each of the solutions was added to basic culture media (the same with that in Test 1) in different concentrations (50, 100, 250, 500, and 1000 ppm) to prepare test cultures and control cultures.

Antibacterial activity was tested for these cultures in the same manner as in test 1.

2) Results

The results are shown in Table 5.

TABLE 5

| sample No. | proliferation inhibition rate (%) quantity of LF hydrolyzate (ppm) | | | | |
|---|---|---|---|---|---|
| | 50 | 100 | 250 | 500 | 1000 |
| 1 | 20 | 78 | 100 | 100 | 100 |
| 2 | 2 | 54 | 96 | 100 | 100 |
| 3 | 0 | 5 | 24 | 78 | 100 |
| 4 | 41 | 97 | 100 | 100 | 100 |
| 5 | 35 | 93 | 100 | 100 | 100 |
| 6 | 16 | 62 | 100 | 100 | 100 |
| 7 | 0 | 3 | 15 | 38 | 61 |
| 8 | 26 | 65 | 84 | 100 | 100 |
| 9 | 0 | 0 | 0 | 0 | 0 |
| 10 | 0 | 0 | 0 | 0 | 0 |

TABLE 5-continued

| sample No. | proliferation inhibition rate (%) quantity of LF hydrolyzate (ppm) | | | | |
|---|---|---|---|---|---|
| | 50 | 100 | 250 | 500 | 1000 |
| control | 0 | 0 | 7 | 25 | 46 |

As will be seen from Table 5, addition of 250 ppm unhydrolyzed LF (control) showed weak antibacterial activity, and complete inhibition against proliferation of E. coli could not be achieved even by ,addition of 1000 ppm of unhydrolyzed LF hydrolyzate having a decomposition rate over 10% obtained from hydrolysis by MOLSIN F, swine pepsin, SUMIZYME AP and AMANO M all of which are acidic proteases, showed potent antibacterial activity at a concentration of only 100 ppm, and a concentration over 250 ppm may inhibit proliferation of coliform bacillae perfectly. On the other hand, LF hydrolyzate resulting from hydrolysis by trypsin which is a neutral protease did not show any antibacterial activity even at a concentration of 1000 ppm.

LF hydrolyzate having a decomposition rate of more than 10% as a result of hydrolysis by acidic proteases has stronger antibacterial activity against coliform bacillus than unhydrolyzed LF.

[TEST 7]

The purpose of this test is to confirm the antibacterial activity of a composition containing a hydrolyzate of metal saturated LF.

The antibacterial activity of hydrolyzates of iron saturated LF was tested in the same manner as in test 5, except that hydrolyzates of iron saturated LF prepared in the same manner as in Example 5 and cow's milk sold in the market were used.

Each of three kinds of samples, to one of which is added hydrolyzate of Fe-LF, to another one of which is added unhydrolyzed LF and the third of which is added nothing, were respectively distributed into 3 test tubes (in total 9) and preserved at 25° C. for observation of any change in appearance.

The results are shown in Table 6.

that hydrolyzate of Fe-LF has excellent antibacterial activity in comparison with unhydrolyzed LF.

[TEST 8]

The purpose of this test is to confirm the antibacterial activity of LF hydrolyzate in the presence of iron.

The antibacterial activity was tested with respect to some samples used in Test 6, i. e. sample Nos. 1, 2, 5, 6 and the sample containing unhydrolyzed LF (control) in the same manner as in Test 6, except that 0.01 mM of ferrous sulfate ($FeSO_4$) was further added to the respective culture media.

The results are shown in Table 7.

TABLE 7

| sample No. | proliferation inhibition rate (%) quantity of LF hydrolyzate (ppm) | | | | |
|---|---|---|---|---|---|
| | 50 | 100 | 250 | 500 | 1000 |
| 1 | 13 | 59 | 100 | 100 | 100 |
| 2 | 0 | 26 | 87 | 100 | 100 |
| 5 | 27 | 65 | 86 | 100 | 100 |
| 6 | 14 | 40 | 93 | 100 | 100 |
| control | 0 | 0 | 0 | 0 | 0 |

The antibacterial activity of unhydrolyzed LF was deactivated in the presence of 0.01 mM of ferrous sulfate. However, all of the LF hydrolyzates resulting from hydrolysis by acidic proteases maintained their antibacterial activity in the presence of 0.01 mM of ferrous sulfate.

Now some tests will be described hereunder for exemplifying the utility of LF hydrolyzate as a tyrosinase inhibition agent.

[TEST 9]

The purpose of this test is to exemplify the tyrosinase inhibition activity of LF hydrolyzate resulting from acid hydrolysis of LF.

1) Preparation of Samples

Native LF sold in the market (by Oleofina, Belgium) was dissolved into purified water in 5% concentration. The resultant solution was divided into several lots which were adjusted into different pH values, 1, 2, 3 and 4 by adding 1M hydrochloric acid thereto. The

TABLE 6

| sample | preservation (day) | | | | |
|---|---|---|---|---|---|
| | 0 | 3 | 7 | 10 | 14 |
| hydrolyzate of FE-LF | | | | | |
| 1 | no change | no change | no change | no change | no change |
| 2 | no change | no change | no change | no change | no change |
| 3 | no change | no change | no change | no change | no change |
| unhydrolyzed Fe-LF ? | | | | | |
| 1 | no change | no change | no change | no change | coagulated |
| 2 | no change | no change | no change | no change | coagulated |
| 3 | no change | no change | no change | no change | coagulated |
| control (added nothing) | | | | | |
| 1 | no change | no change | no change | coagulated | coagulated |
| 2 | no change | no change | no change | no change | coagulated |
| 3 | no change | no change | no change | coagulated | coagulated |

All of the samples (milk) to which was added hydrolyzate of Fe-LF did not show any change in appearance on the 14th day after initiation of the test. All of the samples to which was added unhydrolyzed LF did not show any change in appearance until 10th day after initiation of the test, but all of the samples showed coagulation on the 14th day. In the control samples, 2 samples showed coagulation on the 10th day, and all of the samples coagulated on the 14th day. It is exemplified resultant solutions having different pH values were subjected to hydrolysis reaction under different conditions in a combination of a temperature between 60°–130° C. and a reaction time between 5–60 minutes, to thereby prepare 8 kinds of solutions of LF hydrolyzate having different decomposition rates as shown in Table 8. The resultant solutions were adjusted to pH 7 with 1M sodium hydroxide, then lyophilized to thereby obtain 8 kinds of powdery LF hydrolyzate in different decomposition rates between 4-30%.

2) Method 2-1) Determination of Decomposition Rate

The decomposition rate (%) of the resultant LF hydrolyzate was determined in such a manner that the quantity of formol nitrogen in the respective samples was measured by formol titration method, then the resultant values were applied to the following formula:

$$\text{Decomposition rate} = 100 \times (A/B)$$

(wherein A denotes quantity of formol nitrogen, and B denotes quantity of total nitrogen).

2-2) Measurement of Tyrosinase Inhibition Activity 2-2-1) Preparation of Various Solutions 2-2-1-1) Preparation of Substrate Solution L-tyrosine as guaranteed grade reagent (by Wakoh Junyaku Kogyoh) was dissolved into 0.1M phosphate buffer solution in 0,045% (W/V) concentration.

2-2-1-2) Preparation of Enzyme Solution

Tyrosinase derived from mushroom (by Sigma, 3,000 unit/mg) was dissolved into 0.1M phosphate buffer solution (pH 7.0) in 0.1% (W/V) concentration.

2-2-1-3) Preparation of Copper Ion Solution

Copper sulfate as guaranteed grade reagent (by Wakoh Junyaku Kogyoh) was dissolved into purified water in 1% (W/V) concentration.

2-2-1-4) Preparation of Sample Solution

Each of the solutions of LF hydrolyzate previously prepared in item 1) in different decomposition rates was respectively dissolved into 0.1M phosphate buffer solution (pH 7.0) to prepare sample solutions in 8 different concentrations, so that when the sample solutions were added in the proportions described in the next item 2-2-2), 8 lots of test samples in different concentrations as shown in Table 8 were prepared for each of the LF hydrolyzates having different decomposition rates.

2-2-2) Enzymatic Reaction

Each of the resultant sample solutions, previously prepared substrate solution and the copper ion solution, which are previously heated to 37° C., were mixed in a test tube in the proportions as follows:

sample solution 1.0 ml
substrate solution 0.9 ml
copper ion solution 0.02 ml

To each of the mixtures, 0.08 ml of enzyme solution which was previously heated to the same temperature was added (in total 2.0 ml), and the enzymatic reaction was performed at 37° C. for 3 minutes. After the reaction, 2 ml of 30% acetic acid solution was added to each of the reaction mixtures to terminate the enzymatic reaction, then the absorbancy of the respective reaction mixtures was measured with a spectrophotometer at the wave length of 640 nm (the values of the absorbancy are denoted as B). As a control, a solution was prepared substituting 1.0 ml of 0.1M phosphate buffer solution for the sample solution, and the resultant solution was subjected to the enzymatic reaction and measurement of absorbancy in the same manner as test samples No. 1–No. 8 (the value of the absorbancy of the control is denoted as A). When the sample solution was muddy, the absorbancy of a corresponding mixture which has the same composition as the muddy sample solution in question except that the enzyme solution was substituted with 0.08 ml of 0.1M phosphate buffer solution was measured (the value of the absorbancy is denoted as C), and the value of C is reduced from the value B to obtain the difference of absorbancy of the reaction mixture before and after enzymatic reaction.

The measured values were applied to the following formula to obtain the tyrosinase inhibition rate (%):

$$\text{inhibition rate} = 100 \times [1 - (B - C)/A]$$

3) Results

The results are shown in Table 8.

TABLE 8

| sample No. | decomposition rate (%) | concentration of LF hydrolyzate 0.02 | 0.05 | 0.1 | 0.3 | 0.4 | 0.5 | 1.0 | 2.0 |
|---|---|---|---|---|---|---|---|---|---|
| control | 0 | 0 | 0 | 0 | 0 | 0 | 0 | 0 | 0 |
| 1 | 4 | — | — | 3 | 11 | — | 19 | 30 | 50 |
| 2 | 6 | 11 | 29 | 59 | 80 | — | 100 | — | — |
| 3 | 8 | 9 | 33 | 61 | 79 | — | 100 | — | — |
| 4 | 10 | 16 | 33 | 63 | 85 | — | 100 | — | — |
| 5 | 15 | 10 | 32 | 61 | 81 | — | 100 | — | — |
| 6 | 20 | 9 | 30 | 62 | 77 | — | 100 | — | — |
| 7 | 25 | 9 | 28 | 60 | 82 | — | 100 | — | — |
| 8 | 30 | 13 | 31 | 58 | 81 | — | 100 | — | — |

Note: tyrosinase inhibition rate (%)

Sample No. 1 which had a 4% decomposition rate showed about a 10% tyrosinase inhibition rate with addition of 0.3% of the LF hydrolyzate. The inhibition activity increased as the concentration of LF hydrolyzate increased, such that a 30% inhibition rate was observed with addition to 1% LF hydrolyzate, and a 50% inhibition rate was observed with addition of 2% to the LF hydrolyzate.

On the other hand, Samples No. 2–8 having decomposition rates 6–30% showed about a 30% inhibition rate with addition of LF hydrolyzate only in 0.05% concentration. The inhibition rate increased as the concentration of LF hydrolyzate was increased, and that about a 60% inhibition rate was observed at 0.1% concentration, an 80% inhibition rate was observed at 0.3% concentration, and 100% inhibition was observed at with 0.5% concentration.

It was also confirmed that acid hydrolyzates of other LF substances such as apolactoferrin, zinc-, copper-, and iron-LF showed similar tyrosinase inhibition rates.

[TEST 10]

The purpose of this test is to exemplify the tyrosinase inhibitory efficacy of LF hydrolyzate resulting from enzymatic hydrolysis of LF.

1) Preparation of Sample

LF sold in the market (by Oleofina) was dissolved into purified water in 5% concentration. The resultant LF solution was distributed into 8 lots to which different combinations of enzymes comprising swine pepsin, AMANO A and soy source enzyme containing peptidase sold in the market were added in different concentrations between 0.1–6% to prepare samples Nos. 9–16. The resultant mixtures were kept at 37° C. for different reaction times between 10 minutes–24 hours. The reacted solutions were adjusted to pH 7, heated to 80° C. for 10 minutes for deactivation of enzymes, then lyophilized to obtain LF hydrolyzate having different decomposition rates between 6–50%.

2) Method

Decomposition rates and tyrosinase inhibition rates of the respective LF hydrolyzates were measured in the same manner as in Test 9.

3) Results

The results are shown in Table 9.

TABLE 9

| sample No. | decomposition rate (%) | concentration of LF hydrolyzate (%) | | | | | | |
|---|---|---|---|---|---|---|---|---|
| | | 0.02 | 0.05 | 0.1 | 0.3 | 0.5 | 1.0 | 2.0 |
| control | 0 | 0 | 0 | 0 | 0 | 0 | 0 | 0 |
| 9 | 6 | 10 | 28 | 55 | 82 | 100 | — | — |
| 10 | 10 | 8 | 32 | 60 | 79 | 100 | — | — |
| 11 | 15 | 9 | 33 | 58 | 80 | 100 | — | — |
| 12 | 20 | 12 | 31 | 62 | 78 | 100 | — | — |
| 13 | 30 | 9 | 30 | 61 | 83 | 100 | — | — |
| 14 | 40 | 11 | 28 | 60 | 80 | 100 | — | — |
| 15 | 45 | — | — | 2 | 11 | 23 | 35 | 54 |
| 16 | 50 | — | — | 3 | 10 | 27 | 33 | 52 |

Note: tyrosinase inhibition rate (%)

Sample Nos. 9–14 which had a decomposition rate between 6–40% showed about a 30% tyrosinase inhibition rate with addition of 0.05% LF hydrolyzate. The inhibition activity increased as the concentration of LF hydrolyzate increased. About a 60% inhibition rate was achieved with addition of 0.1% LF hydrolyzate, about 80% inhibition rate with addition of 0.3% LF hydrolyzate, and 100% inhibition rate with addition of 0.5% LF hydrolyzate.

On the other hand, Sample Nos. 15 and 16 having decomposition rates of 45 and 50% respectively showed about a 10% inhibition rate at 0.3% concentration of LF hydrolyzate. The inhibition rate increased as the concentration of LF hydrolyzate was increased, such that about a 30% inhibition rate was achieved at 1% concentration, and about a 50% inhibition rate at 2% concentration.

It was also confirmed that enzymatic hydrolyzate of other LF substances, that is apolactoferrin, metal saturated LF chelated with metals such as zinc, copper, iron and the like showed substantially the same tyrosinase inhibition rate. More specifically it was found that the tyrosinase inhibition rate mainly depends upon the decomposition rate of LF hydrolyzate.

Now, some examples will be described for better understanding of the present invention.

EXAMPLE 1

To 950 g of purified water, 50 g of native LF sold in the market (by Oleofina, Belgium) was dissolved, then the pH of the solution was adjusted to 2 with 1M hydrochloric acid. The resultant solution was heated to 120° C. for 15 minutes for acid hydrolysis, then cooled, thereby about 1000 g of a 5% solution of LF hydrolyzate having antibacterial activity was obtained. The decomposition rate of the LF hydrolyzate was 9% (determined by the same method as in Test 1).

EXAMPLE 2

To 850 g of purified water, 150 g of native LF sold in the market (by Oleofina, Belgium) was dissolved. The resultant solution was adjusted to pH 3 with 1M citric acid, then heated to 130° C. for 60 minutes for hydrolysis. The resulting solution was cooled, adjusted to pH 7 with 1M sodium hydroxide, filtered, demineralized, then lyophilized (freezedried) thereby about 45 g of powdery LF hydrolyzate having antibacterial activity was obtained.

The decomposition rate of this LF hydrolyzate was 12% (determined by the same method as in Test 1).

EXAMPLE 3

1) Preparation of Fe Saturated LF

To 180 g of purified water, 20 g of native LF sold in the market (by Oleofina, Belgium) was dissolved. To the resultant solution, 200 mg of $FeSO_4.7H_2O$ was added. After maintaining at 25° C. for 12 hours, unreacted Fe was removed from the reacted solution by ultrafiltration module SEP-1013 (trademark, by Asahikasei), then the resultant filtrate was lyophilized to thereby obtain about 19 g of iron saturated LF.

2) Hydrolysis of Fe Saturated LF

To 285 g of purified water, 15 g of iron saturated LF was dissolved, the pH of the resulting solution was adjusted to 1.0 with 2M hydrochloric acid, heated at 90° C. for 15 minutes for hydrolysis, then cooled, thereby yielding about 300 g of about 5% solution of LF hydrolyzate having antibacterial activity.

The decomposition rate of the resulted LF hydrolyzate was 7% (determined by the same method as in Test 1).

EXAMPLE 4

1) Preparation of Column

In a column (id. 10 cm), 500 ml of SEPABEADS FP-CM13 (trademark, by Mitsubishi Kasei) having a carboxymethyl group as an ion-exchange group was placed, then a 10% aqueous solution of sodium chloride was passed through the resulting column. The column was washed with water to thereby obtain a Na-type ion-exchnager.

2) Preparation of Native LF

To the resultant column, 60 l of cheese whey (pH 6.5) originated from goat milk was introduced at 4° C. at the flow rate of 4 l/hour. After the column was washed with water to remove the unadsorbed components of the cheese whey, the adsorbed component of the cheese whey was eluted with a 10% aqueous solution of sodium hydroxide at the flow rate of 5 l/hour to thereby obtain about 5 l of eluate. The resultant eluate was concentrated with ultrafiltration module SEP-1013 (trademark, by Asahikasei) then water was added thereto to remove sodium chloride to thereby obtain about 200 ml of LF solution containing 1% goat LF.

3) Acid Hydrolysis

The resultant LF solution was adjusted to pH 2.0 with 1M hydrochloric acid, heated to 120° C. for 20 minutes, then cooled, to thereby obtain about 200 g of a 1% solution of LF hydrolyzate having antibacterial activity. The decomposition rate of the LF hydrolyzate was 10% (determined by the same method as in Test 1).

EXAMPLE 5

1) Preparation of Fe Saturated LF

To 9 kg of purified water, 1 kg of native LF (by Oleofina, Belgium) was dissolved. To the resultant solution, 10 g of $FeSO_4.7H_2O$ was added, and maintained at 25° C. for 12 hours. From the resultant solution, unreacted iron was removed by ultrafiltration module SEP-1013 (trademark, by Asahikasei).

2) Enzymatic Hydrolysis

After adjusting the resultant solution to pH 3.5 with 0.5N hydrochloric acid, 10 g of MOLSIN F (trademark, by Seishin Seiyaku, 42,000 unit/g of protein) sold in the market was added to the solution and homogeneously mixed. The resultant mixture was maintained at 37° C. for 180 minutes, neutralized, heated to 85° C. for 10 minutes for deactivation of the enzyme, then cooled, thereby yielding about 10 kg of LF hydrolyzate solution having antibacterial activity.

The decomposition rate of the resultant LF hydrolyzate was 13.5% (determined by the same method as in Test 1).

EXAMPLE 6

To 9 kg of purified water, 1 kg of native LF (by Oleofina, Belgium) was dissolved. The resultant solution was adjusted to pH 2.5 with 2M citric acid, then 30 g of swine pepsin sold in the market was added (10,000 unit/g of protein: by Wakoh Junyaku Kogyo), homogeneously mixed, maintained at 37° C. for 180 minutes for hydrolysis, heated to 85° C. for 10 minutes for deactivation of the enzyme, cooled, then concentrated by the conventional method to thereby obtain about 10 kg of a solution of the LF hydrolyzate having antibacterial activity.

The decomposition rate of the resultant LF hydrolyzate was 11.3% (determined by the same method as in Test 1).

EXAMPLE 7

1) Preparation Cu Saturated LF

Copper saturated LF was prepared as follows. To 50 l of goat skim milk, 5 l of 0.1M citric acid solution containing 0.003M ferric chloride ($FeCl_3$) was added and homogeneously mixed. To the resultant solution, 5 l of CM-Sephadex C-50 ($H^+$ type, by Pharmacia) was added and stirred for 1 hour. After removing unadsorbed components of the goat skim milk by washing the ion-exchange resin with water, the resin was suspended in 0.05M tris-hydrochloride buffer solution (pH 8.0). The resultant suspension was placed in a column (20×50 cm), then washed with the same buffer solution. The adsorbed components of goat skim milk were eluted with 0.05M tris-hydrochloric acid buffer solution containing sodium chloride in a gradient of 0–2M to thereby collect about 800 ml of an LF-containing fraction. The resultant LF-containing fraction was concentrated to 150 ml with ultrafiltration membrane PM-10 (trademark, by Amicon), then dialyzed against 0.05M tris-acetate buffer solution (pH 8.2) containing 0.5M sodium chloride. The resultant dialyzed solution was introduced into a column (10×30 cm) filled with copper chelating SEPHAROSE 6B (trademark, by Pharmacia) which was previously equilibrated with the same buffer solution to adsorb LF. After washing the column with the same buffer solution, the adsorbate was eluted with acetate buffer solution (pH 4.0) containing 0.5M sodium chloride. The resultant eluate was dialyzed against purified water, then lyophilized to thereby obtain about 2 g of powdery LF.

2) Enzymatic Hydrolysis

To 17 g of purified water, 2 g of the resulting powdery LF was added. The resultant solution was adjusted to pH 3.5 With 1M lactic acid. To the resultant solution, 60 mg of SUMIZYME AP sold in the market (trademark, by Shinnihon Kagakukougyo, 50,000 unit/g of protein) was homogeneously added, maintained at 50° C. for 180 minutes, neutralized, then the resultant reaction mixture was heated to 85° C. for 10 minutes for deactivation of the enzyme, cooled, concentrated then lyophilized to thereby obtain about 2 g of powdery LF hydrolyzate having antibacterial activity.

The decomposition rate of the resulted LF hydrolyzate was 13.8% (determined by the same method as in test 1).

EXAMPLE 8

An LF solution was prepared by dissolving 80 g of LF sold in the market (by Oleofina) into 1000 ml of purified water, then the pH of the resultant LF solution was adjusted to 2 with 1M hydrochloric acid. The resultant solution was heated to 115° C. for 10 minutes, adjusted to pH 7 with 1M sodium hydroxide solution, then lyophilized to thereby obtain about 77 g of LF hydrolyzate powder having a 15% decomposition rate as measured by the same method as in Test 1.

Having homogeneously mixed 50 g of the resultant LF hydrolyzate, 900 g of glycine (by Wakoh Junyaku Kogyo), and 50 g of lysozyme (by Wakoh Junyaku Kogyo), about 1000 g of a tyrosinase inhibition agent to be used for keeping freshness of food was prepared.

The tyrosinase inhibition rate of a 20% aqueous solution of the resultant tyrosinase inhibition agent was 100% as measured in the same method as in Test 9.

EXAMPLE 9

After dissolving 270 g of LF sold in the market (by Oleofina) into 6300 ml of purified water, the pH of the resultant solution was adjusted to 2.5 with a 10% aqueous solution of citric acid, and kept at room temperature for 1 hour for removal of iron. The reacted solution was subjected to ultrafiltration, and the resultant concentrate was lyophilized to thereby obtain about 260 g of apolactoferrin.

Sixty g of the resultant apolactoferrin was dissolved into 1000 ml of water, and the resultant solution was adjusted to pH 3 with 2M phosphoric acid solution. The resultant solution was heated to 121° C. for 25 minutes, its pH adjusted to 7 with 1M sodium hydroxide solution, then lyophilized to thereby obtain about 55 g of powdery LF hydrolyzate having a 23% decomposition rate as measured by the same method as in Test 9.

Having homogeneously mixed 20 g of the resultant LF hydrolyzate, 400 g of propylene glycol (by Wakoh Junyaku Kogyo), 4 g of oleyl alcohol (by Wakoh Junyaku Kogyo), 200 g of ethanol (by Wakoh Junyaku Kogyo) and 3376 g of purified water, about 4000 g of tyrosinase inhibition agent for use in cosmetics was obtained.

The apparent inhibition rate against tyrosinase of the resultant agent was 75%, but a substantial inhibition rate against tyrosinase was calculated to be 100% in consideration of LF hydrolyzate concentration.

EXAMPLE 10

Having homogeneously mixed 100 g of LF sold in the market (by Oleofina) and 1000 ml of purified water, the pH of the resultant solution was adjusted to 2 with 1M hydrochloric acid. To the resultant solution, 5 g of swine pepsin sold in the market (by Wakoh Junyaku Kogyo) was added and reacted at 37° C. for 60 minutes. The reacted solution was heated to 80° C. for 10 minutes for deactivation of the enzyme, then lyophilized to thereby obtain about 95 g of LF hydrolyzate having a 12% decomposition rate as measured by the same method as in Test 9.

About 2000 g of a tyrosinase inhibition agent for cosmetic use was prepared by homogeneously mixing 30 g of the resultant LF hydrolyzate, 200 g of propylene glycol (by Wakoh Junyaku Kogyo), 2 g of oleyl alcohol (by Wakoh Junyaku Kogyo), 100 g of ethanol (by Wakoh Junyaku Kogyo) and 1668 g of purified water.

The tyrosinase inhibition rate of the resultant tyrosinase inhibition agent was 100% as measured by the same method as in Test 9.

EXAMPLE 11

One hundred and fifty g of LF sold in the market (by Oleofina) was dissolved into 150 g of purified water, the pH of the resultant solution was adjusted to 6 with 1M sodium hydroxide solution, then the solution was pasteurized at 60° C. for 10 minutes. The resultant solution was cooled to 50° C., and 15 g of trypsin (by Nobo) and 30 g of soy sauce enzyme containing peptidase sold in the market (by Tanabe Seiyaku) were added and reacted at 50° C. for 5 hours. The reacted solution was heated at 80° C. for 10 minutes for deactivation of the enzymes, then lyophilized to thereby obtain about 145 g of powdery LF hydrolyzate having a 38% decomposition rate as measured by the same method as in Test 9.

Having homogeneously mixed 12 g of sodium hyaluronate (by Wakoh Junyaku Kogyo), 15 g of placenta extract (by Botoger, West Germany), 10 g of glycerin (by Wakoh Junyaku Kogyo) and 962 g of purified water, about 1000 g of tyrosinase inhibition agent was obtained.

The tyrosinase inhibition rate of the resultant agent was 100% as measured by the same method as in Test 9.

EXAMPLE 12

About 78 g of Fe-LF was prepared by dissolving 90 g of LF sold in the market (by Oleofina) into 2100 ml of purified water, then reacting with 755 ml of a 2.6 mM aqueous solution of ferrous sulfate at room temperature for 24 hours. The resultant reacted solution was subjected to ultrafiltration, then the resultant concentrate was lyophilized.

Forty g of the resultant Fe-LF was dissolved into 500 ml of purified water, and the pH of the resultant solution was adjusted to 3 with 1M hydrochloric acid solution. To the resultant solution, 5 g of SUMIZYME AP (by Shin Nihon Kagaku) was added and the resultant mixture was subjected to hydrolysis at 30° C. for 3 hours. The reacted mixture was heated at 80° C. for 10 minutes for deactivation of the enzyme, then lyophilized to thereby obtain about 35 g of LF hydrolyzate having an 18% decomposition rate as measured by the same method as in Test 9.

About 500 g of a tyrosinase inhibition agent to be used for keeping freshness of food was prepared by homogeneously mixing 30 g of the resultant LF hydrolyzate, 450 g of glycine (by Wakoh Junyaku Kogyo), and 20 g of lysozyme (by Wakoh Junyaku Kogyo).

The tyrosinase inhibition rate of a 20% aqueous solution of the resultant agent was 100% measured as by the same method as in Test 9.

EFFECTS OF THE INVENTION

The effects of the present invention are as follows:
1) The LF hydrolyzates for use as an antibacterial and/or tyrosinase inhibition agent of the present invention are safe for humans and animals, since it is a natural antibacterial and/or tyrosinase inhibitory substance derived from hydrolysis of milk components and the like.
2) The LF hydrolyzates for use as an antibacterial and/or tyrosinase inhibition agent of the present invention have much stronger antibacterial activity than unhydrolyzed LF and have remarkably potent tyrosinase inhibition activity.
3) The LF hydrolyzates for use as an antibacterial and/or tyrosinase inhibition agent of the present invention are stable to heating, and can be provided in liquid and powdery forms, thus it has wider application.
4) The antibacterial and/or tyrosinase inhibition agent comprising LF hydrolyzate of the present invention can be prepared by mixing them with one or more of excipients or other medicines, inclusive of other antibacterial agents and/or other tyrosinase inhibition agents.
5) The antibacterial agent and the tyrosinase inhibition agent consisting of or comprising LF hydrolyzate of the present invention can be utilized as a component of various products such as cosmetics, foods, feeds and other products which are desirable to be prevented or inhibited from qualitative deterioration due to proliferation of microorganisms and/or undesirable effects of tyrosinase activity. It is specifically noted that inclusion of the antibacterial and/or tyrosinase inhibition agent consisting of or comprising LF hydrolyzate of the present invention in such products is effective not only for preservation of the products, but also is effective for therapy or prevention of bacterial infection and/or pigmentation of melanine when the products are given to humans and other animals or applied to the body surface thereof.
6) The antibacterial and/or tyrosinase inhibition agent consisting of or comprising LF hydrolyzates of the present invention can be utilized for treatment of various materials, for example washing or dipping the materials in a solution of the agent so that the agent adheres to or is coated onto or impregnated into those materials, for maintenance of sanitary conditions and for prevention from deterioration in freshness thereof. It is specifically noted that the materials treated are also effective for therapy and prevention against bacterial infection or pigmentation of melanine when they are taken into or applied onto the body surface of human or animals subject to the condition that an effective amount of LF hydrolyzate is accompanied therewith (or remained therein).

What is claimed is:

1. Lactoferrin hydrolyzate, obtained by hydrolyzing lactoferrin at a pH of from 1 to 4, such that said lactoferrin hydrolyzate has a decomposition rate of 6–20%.

2. The lactoferrin hydrolyzate of claim 1, wherein said hydrolyzing is conducted at a temperature of from 80° to 130° C.

3. The lactoferrin hydrolyzate of claim 2, wherein said heating for a length of time of from 1 to 120 minutes.

4. The lactoferrin hydrolyzate of claim 1, having antibacterial and tyrosinase inhibition activities.

5. Lactoferrin hydrolyzate, obtained by enzymatically hydrolyzing lactoferrin with an acidic enzyme at a pH of from 1 to 4, such that said lactoferrin hydrolyzate has a decomposition rate of 6–20%.

6. The lactoferrin hydrolyzate of claim 4, wherein said enzyme is swine pepsin.

7. The lactoferrin hydrolyzate of claim 4, wherein said hydrolyzing is conducted at a pH of from 2 to 3.

8. The lactoferrin hydrolyzate of claim 4, wherein said hydrolyzing is conducted at a temperature of from 15° to 55° C.

9. The lactoferrin hydrolyzate of claim 2, wherein said hydrolyzing is conducted for a length of time of from 30 to 600 minutes.

10. An antibacterial composition comprising the lactoferrin hydrolyzate of claim 1 in an excipient, medicine, cosmetic, food, feed or solution, said lactoferrin hydrolyzate being present in 25–1,000 parts per million, by weight of the composition.

11. An antibacterial composition comprising the lactoferrin hydrolyzate of claim 5 in an excipient, medicine, cosmetic, food, feed or solution, said lactoferrin hydrolyzate being present in 25–1,000 parts per million by weight of the composition.

* * * * *